(12) United States Patent
Tseng et al.

(10) Patent No.: US 9,823,270 B2
(45) Date of Patent: Nov. 21, 2017

(54) MEMBRANE ELECTROCHEMICAL SIGNAL DETECTION SYSTEM

(71) Applicant: National Tsing Hua University, Hsinchu (TW)

(72) Inventors: Fan-Gang Tseng, Hsinchu (TW); Yi Chuan Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 282 days.

(21) Appl. No.: 14/691,190

(22) Filed: Apr. 20, 2015

(65) Prior Publication Data
US 2015/0300978 A1  Oct. 22, 2015

(30) Foreign Application Priority Data
Apr. 21, 2014 (TW) .............................. 103114367 A

(51) Int. Cl.
*G01Q 60/30* (2010.01)
*G01Q 60/40* (2010.01)
*G01N 33/543* (2006.01)

(52) U.S. Cl.
CPC ......... *G01Q 60/30* (2013.01); *G01N 33/5438* (2013.01); *G01Q 60/40* (2013.01)

(58) Field of Classification Search
CPC ........ G01Q 60/30; G01Q 60/40; G01Q 60/60; G01Q 80/00
See application file for complete search history.

(56) References Cited

U.S. PATENT DOCUMENTS

| | | | | |
|---|---|---|---|---|
| 5,874,668 A * | 2/1999 | Xu | ......... | B82Y 35/00 73/105 |
| 8,329,451 B2 * | 12/2012 | Nakatani | .......... | G01N 33/48728 435/283.1 |
| 2006/0213259 A1 * | 9/2006 | Prinz | ..................... | B82Y 35/00 73/104 |
| 2009/0100554 A1 * | 4/2009 | Arnold | ................... | B82Y 35/00 850/39 |
| 2009/0253589 A1 * | 10/2009 | Muller | ................... | B82Y 35/00 506/12 |
| 2010/0261615 A9 * | 10/2010 | Park | ..................... | B82Y 35/00 506/9 |

(Continued)

OTHER PUBLICATIONS

Lin, Yi-Ying, Fan, Shih-Kang, "Formation of Hydrogel-Supported Asymmetric Bilayer Lipid Membrane Between Electrowetting-Driven Encapsulated Droplets." National Tsing Hua University Library, 2011.*

(Continued)

*Primary Examiner* — Wyatt Stoffa
(74) *Attorney, Agent, or Firm* — Muncy, Geissler, Olds & Lowe, P.C.

(57) ABSTRACT

The present invention is related to a membrane electrochemical signal detection system, which comprises a detection platform and a probe, wherein the detection platform comprises a substrate having a cavity; a hydrogel layer disposed in the cavity of the substrate; and a carrier film disposed above the substrate and the hydrogel layer with at least one through hole corresponding to the cavity of the substrate as a sample slot. The surface of the probe is covered by an insulating layer and a metal for detection is exposed at a tip portion of the probe.

9 Claims, 3 Drawing Sheets

(56) References Cited

U.S. PATENT DOCUMENTS

2014/0134336 A1* 5/2014 Ha .................. G03F 7/0002
427/256
2016/0139177 A1* 5/2016 Tseng .................. G01Q 70/14
435/18

OTHER PUBLICATIONS

Roerdink Lander, Monique, Sania Ibragimova, Christian Rein, Jorg Vogel, Karin Stibius, Oliver Geschke, Mark Perry, and Claus Hélix-Nielsen. "Biomimetic membrane arrays on cast hydrogel supports." Langmuir 27, No. 11 (2011): 7002-7007.*

Ibragimova, Sania, Karin Bagger Stibius Jensen, Piotr Przemyslaw Szewczykowski, Mark Perry, Henrik Bohr, and Claus Helix Nielsen. "Hydrogels for in situ encapsulation of biomimetic membrane arrays." Polymers for Advanced Technologies 23 (2012): 182-189.*

Fan-Gang Tseng, Yi-Quan Chen, Selfassembly of Lipid Bilayer on Nano/Micro Pore Applied to Detection of Membrane Proteins by Atomic Force Microscopy, National Tsing Hua University Library, 2008, 7 pages.

Lin, Yi-Ying, Fan, Shih-Kang, Formation of Hydrogel-Supported Asymmetric Bilayer Lipid Membrane Between Electrowetting-Driven Encapsulated Droplets, National Tsing Hua University Library, 2011, 9 pages.

Patrick L T M Frederix, Maurizio R Gullo, Terunobu Akiyama, Andreas Tonin, Nicolaas F De Rooij, URS Staufer and Andreas Engel, Assessment of Insulated Conductive Cantilevers for Biology and Electrochemistry, Nanotechnology 16 (2005)997-1005.

\* cited by examiner

MEMBRANE ELECTROCHEMICAL SIGNAL DETECTION SYSTEM

BACKGROUND OF THE INVENTION

1. Field of the Invention

The present invention relates to a membrane electrochemical signal detection system, more particularly, the present invention relates to a membrane electrochemical signal detection system for detecting an electrochemical physiological signal of a membrane protein.

2. Description of Related Art

In any organism, the cell membrane transports many kinds of substances to regulate various physiological functions. As a result, the studies about cell membrane are widely conducted by many researchers from the entire world. Cells are isolated systems since the cell membrane isolates the inner and outer environments of the cells. Therefore, the transportation of substances between the inner and outer sides of the cell membrane is an interesting bio-energy phenomenon.

For example, in cellular respiration and photosynthesis, energy is generated in an organism through the ability to capture the ion flow across the cell membrane. The ion flow will cause voltage differences that will allow active transportation of substances and cell migration.

The constant pH value in an organism is maintained by the proton pumps of the cell membrane. These proton pumps are able to control the input and output of the protons to produce different proton gradients inside and outside of the cell membrane. The differences in the pH values of the cytoplasm and organelles are the energy sources for many biological reactions.

Energy is required for the transportation of substances by membrane proteins. Such an energy source can be provided by the proton gradient or the active transporting pumps (such as H+ATPase) of the cell membrane. The transportation of substances across the cell membrane may be performed by exchanging substances across the cell membrane.

The purposes of the transportation mechanisms described above are to maintain the ionic homeostasis within the cytoplasm and to regulate the metabolism in organisms. The acid-base gradient within the cytoplasm plays an important role as a driving force for the transportation of nutrients from the outside of the cells to the inside of the cells. Thus, the studies of the structures and the reaction mechanisms of the membrane proteins as well as the transportation of the coupled protons have drawn the attentions of many researchers for further investigations.

However, the studies of the membrane protein transport channels are often accompanied by difficulties in the positioning of the membrane proteins and in the confirmation of the membrane protein structures. Consequently, the electrochemical physiological signals from both sides of the membrane proteins are often detected from a large area of the membrane surface. It is often difficult to detect a single membrane protein or a specific area on the cell membrane. Hence, a more accurate detection system is needed to study the mechanisms for the transportation of substances by membrane proteins.

SUMMARY OF THE INVENTION

The object of the present invention is to provide a membrane electrochemical signal detection system, which is used to detect the physiological mechanism of the transport by membrane protein, the structure of the proton transport channel, and the titration of transport. The membrane electrochemical signal detection system of the present invention comprises a detection platform and a probe, wherein the detection platform comprises: a substrate having a cavity; a hydrogel layer disposed in the cavity of the substrate; and a carrier film disposed above the substrate and the hydrogel layer with at least one through hole corresponding to the cavity of the substrate as a sample slot. The surface of the probe is covered by an insulating layer and a metal for detection is exposed at a tip portion of the probe.

In the membrane electrochemical signal detection system of the present invention, the substrate of the detection platform can be made of silicon, silicon oxide, silicon nitride, or the like, wherein silicon is preferred.

In the detection platform, the opening of the cavity formed on the substrate may face toward the carrier film or the cavity may be a through hole that extends through the substrate. The area for the opening of the cavity may be 50 $\mu m^2 \sim 2$ $mm^2$ and is preferred to be 500 $\mu m^2 \sim 1$ $mm^2$. The hydrogel layer may be disposed in the cavity and be composed by a polymer hydrogel. The hydrogel layer may be selected from the group consisting of polyethylene (glycol) diacrylate (PEGDA), poly(ethylene glycol) diacrylate, agarose gel, polyacrylamide gel (PAG), and sodium dodecyl sulfate polyacrylamide gel (SDS-PAG). The carrier film may be disposed above the substrate and the hydrogel layer, and has at least one through hole corresponding to the cavity of the substrate as a sample slot. A gap between the hydrogel layer and the carrier film may be 50 nm~1 μm and is preferred to be 100 nm~200 nm. The thickness of the carrier film may be 20 nm~500 nm and is preferred to be 50 nm~200 nm. The volume of the sample slot may be 0.1 nL~10 nL and is preferred to be 0.1 nL~5 nL. The carrier film may be selected from the group consisting of $SiO_2$, $Si_3N_4$, and $HfO_2$, wherein $Si_3N_4$ is preferred.

In the detection system of the present invention, the surface of the probe is covered by an insulating layer and a metal for detection is exposed at a tip portion of the probe. The insulating layer may be formed by plasma enhanced chemical vapor deposition or atomic layer deposition. The thickness of the insulating layer may be 10 nm~100 nm and is preferred to be 10 nm~30 nm. The metal for detection exposed at a tip portion of the probe may be selected from the group consisting of platinum, iridium, cobalt, palladium, rhodium, and alloys thereof, wherein platinum or platinum/iridium is preferred. The surface area of the metal for detection exposed at a tip portion of the probe may be 100 $nm^2 \sim 2$ $\mu m^2$ and is preferred to be 500 $nm^2 \sim 1$ $\mu m^2$.

The detection system of the present invention may further comprise an atomic force microscope, wherein a scanning process thereof is performed by the probe in order to locate the membrane proteins.

The detection system of the present invention may further comprise a power supply, which provides a current signal or a voltage signal to the probe.

The detection system of the present invention may further comprise an electrode, which is disposed beneath the hydrogel layer to receive the current signal or the voltage signal released by the probe.

According to an embodiment of the membrane electrochemical signal detection system of the present invention, a self-assembled lipid bilayer is formed in the nano/micro scale sample slots of the detecting platform by using a Langmuir-Blodgett Trough. The electrophysiological signals at the inner and outer sides of the membrane are then detected by the atomic force microscope with the modified probe.

Overall, the membrane electrochemical signal detection system of the present invention provides a detection platform. Lipid membranes may form effectively and be maintained stably on the platform. A scanning process is performed by the atomic force microscope with the modified probe provided by the present invention. The membrane proteins on the lipid membranes may be positioned accurately. The modified probe provided by the present invention has a nano-scale metal tip portion. This allows the area of the lipid membranes for the detection of the electro-physiological signals to narrow to a specific region. The electro-physiological signals at the inner and outer sides of the lipid membranes can be detected with the noises from the other regions being effectively reduced.

Accordingly, the present invention is useful for the investigations of the mechanisms for the ion flow, the protein channels, the water channels, or the nerve conduction channels of different membrane proteins. Any unknown biochemical models may be clarified. Therefore, the membrane electrochemical signal detection system provided by the present invention may be used as a novel biological and medical detection device. Such invention may have potential for development in the medical device industry.

DETAILED DESCRIPTION OF THE PREFERRED EMBODIMENT

Preparation Example 1—Preparation Method of the Detection Platform

Figure 1:
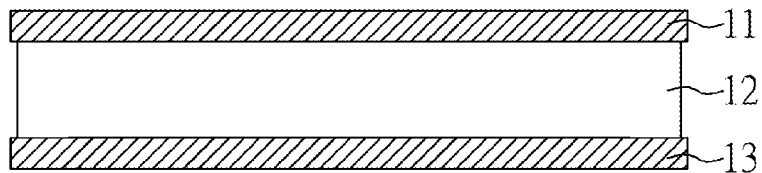
FIGS. 1 to 8 are schematic diagrams showing the preparation method of the detection platform in preparation example 1.
Figure 2:
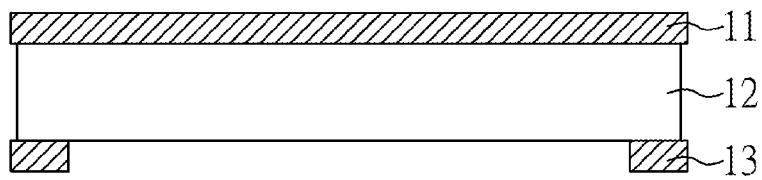
Figure 3:
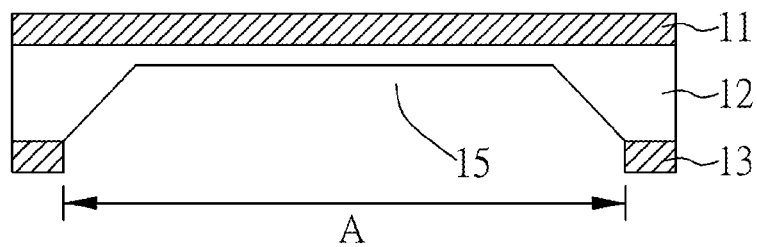
Figure 4:
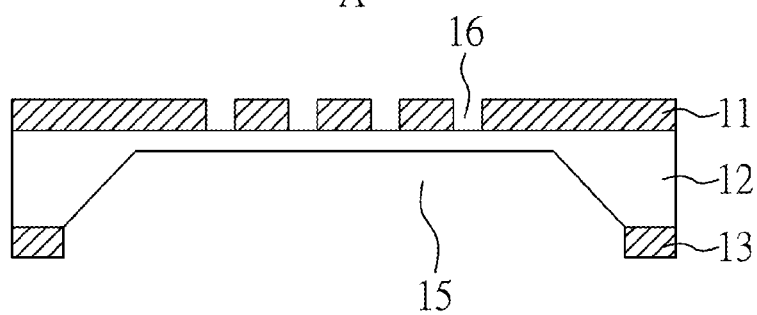
Figure 5:
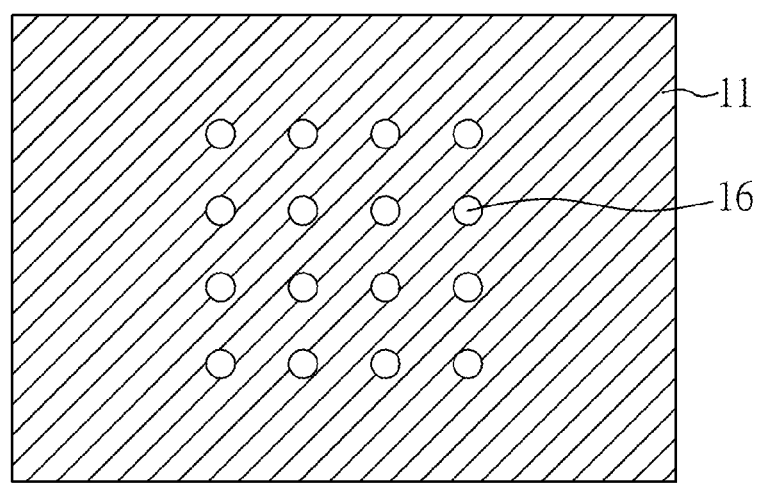
Figure 6:
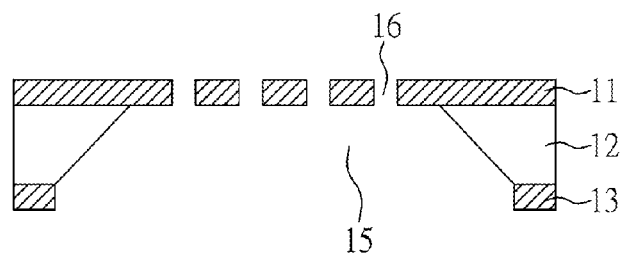
Figure 7:
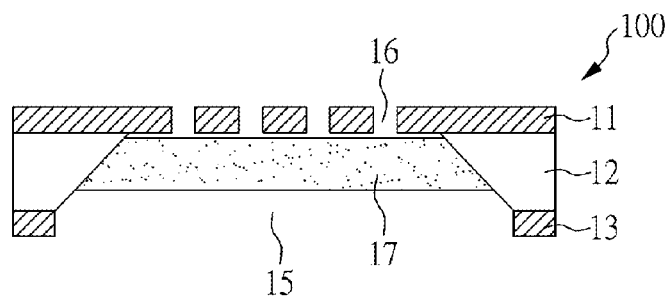

First, as shown in FIG. 1, a silicon substrate 12 is provided with its upper and lower surfaces coated with two low stress silicon nitride layers ($SiN_4$) 11 and 13 each with a thickness of 50 nm~200 nm. The silicon nitride layer 11 is served as a carrier film. Second, as shown in FIG. 2, the silicon nitride layer 13 beneath the silicon substrate 12 is dry etched using reactive ion beam etching (RIE). Portions of the silicon substrate 12 are exposed. Third, as shown in FIG. 3, the silicon substrate 12 is immersed in a wet-etching solution (KOH). A cavity 15 was formed by wet etching the exposed portions of the silicon substrate 12. The area A of the cavity 15 may be 50 $\mu m^2$~2 $mm^2$, wherein the area of the cavity 15 is the area of the bottom side (opening) of the cavity 15. Fourth, as shown in FIG. 4, one or more nano/micro scale through holes corresponding to the cavity 15 are formed as sample slots 16 across the silicon nitride layer 11 above the silicon substrate 12 using focused ion beam lithography. The size and shape of the through holes can be controlled by electron beam lithography. As shown in FIG. 5, which is the top view of FIG. 4, the shape of the sample slot 16 is not particularly limited; however, circular shape is preferred. The volume of the sample slot 16 may be 0.1 nL~5 nL. Fifth, as shown in FIG. 6, the silicon substrate 12 below the carrier film 11 is immersed in a wet etching solution (KOH). The portions of the silicon substrate 12 below the carrier film 11 are removed by etching. Sixth, as shown in FIG. 7, a polymer hydrogel is injected into the cavity 15 from the bottom of the silicon substrate 12. A hydrogel layer 17 is formed by curing the polymer hydrogel with UV light irradiation. A gap a between the carrier film 11 and hydrogel layer 17 may be 50 nm~1 μm. The resulting detection platform 100 is shown in FIG. 7.

Figure 8:
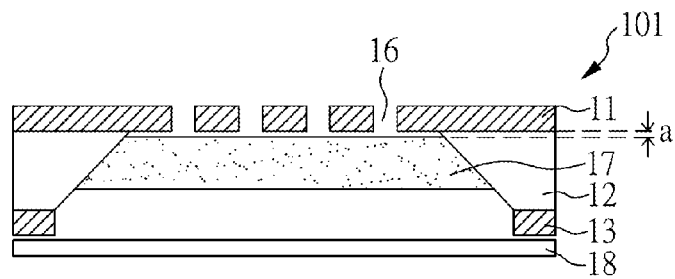

In addition, an electrode 18 may be disposed under the detection platform 100 shown in FIG. 7. The resulting detection platform 101 is shown in FIG. 8. The electrode 18 receives the current signals or voltage signals from the samples in the sample slots to analyze the electro-physiologic signals at the inner and outer sides of the membrane proteins.

Preparation Example 2—Preparation Method for the Probe

Figures 9, 10, 11:
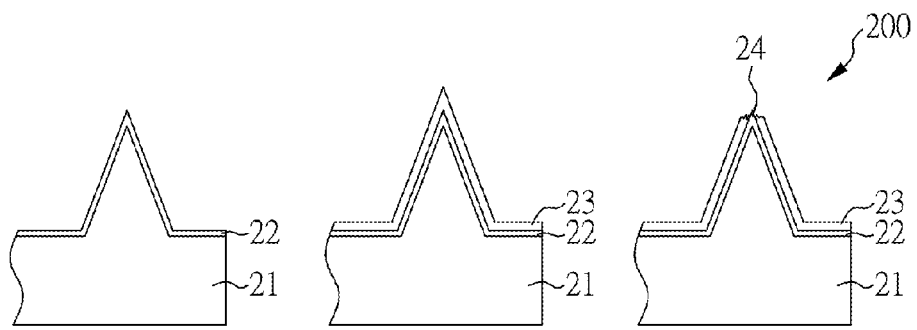
FIGS. 9 to 11 are schematic diagrams showing the preparation method of the probe in preparation example 2.

First, as shown in FIG. 9, a metal layer 22 is coated on the surface of a probe 21 of an atomic force microscope. The probe 21 may be any probes of any atomic force microscopes known in the art and the material of the probe 21 is not particularly limited. The metal layer 22 may be selected from the group consisting of platinum, iridium, cobalt, palladium, rhodium, and alloys thereof. The thickness of the metal layer 22 may be 5 nm~20 nm. Next, as shown in FIG. 10, an insulating layer 23 is deposited on the surface of the metal layer 22. The insulating layer 23 may be selected from the group consisting of $SiO_2$, $Si_3N_4$, $HfO_2$, and other insulating materials known in the art. The thickness of the insulating layer 23 may be 10 nm~30 nm. In the present preparation example, the insulating layer 23 may be deposited on the metal layer 22 by atomic layer deposition (ALD). However, in other embodiments, other methods such as plasma enhanced CVD (PECVD) or physical vapor deposition (PVD) may be applied to deposit the insulating layer 23 on the metal layer 22. Then, the probe is installed in an atomic force microscope. A scanning process is executed repeatedly on a hard material where the tip of the probe and the hard material are in repeated scuffing against each other. The insulating layer 23 on the tip portion of the probe is rubbed off until an appropriate area 24 of the metal layer 22 beneath the insulating layer 23 is exposed at the tip portion of the probe. The exposed portion 24 of the metal layer 22 at the tip portion of the probe may have an area of 500 $nm^2$~1 $\mu m^2$. The resulting probe 200 is shown in FIG. 11.

Example 1

The present example demonstrates a method for detecting the electro-physiological signals at the inner and outer sides of the membrane proteins by using the detection platform and the probe from the preparation examples 1 and 2, respectively.

In the present example, lipid molecules 322 self-assembled into a lipid bilayer 32 in the sample slot of the detection platform 101 by using a Langmuir-Blodgett Trough. The protein tested is a proton-pumping pyrophosphatase ($H^+$-PPase) which is a membrane protein channel 321 formed across the lipid bilayer 32. Hydrogen ions are capable of passing in and out of the lipid bilayer 32 through this membrane protein channel 321.

The probe 200 is then installed in an atomic force microscope. A conductive electrical wire (not shown) connects the back end of the probe 200 to a power supply (not shown) and an oscilloscope (not shown).

Figure 12:
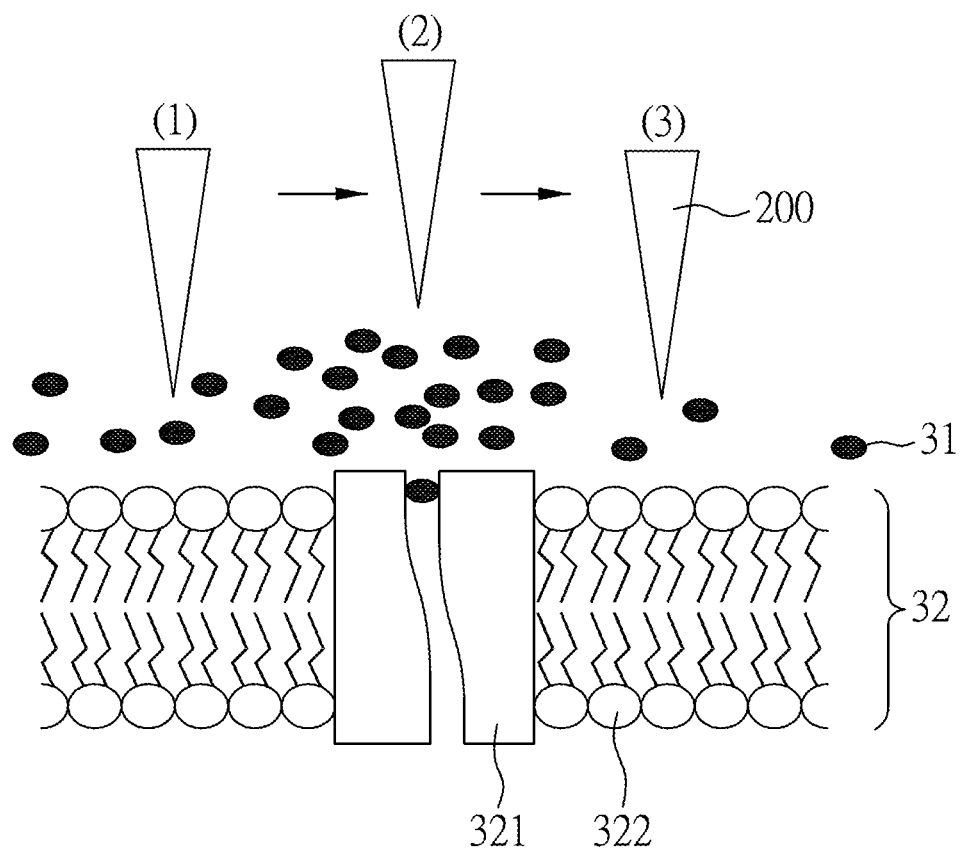
FIG. 12 is a schematic diagram showing the method for positioning the membrane protein in a preferred embodiment of the present invention.

As shown in FIG. 12, the lipid bilayer 32 is scanned by an atomic force microscope. The membrane protein channel 321 located across the lipid bilayer 32 is still active, so hydrogen ions (H⁺) 31 are being transported. When the hydrogen ions 31 are transported by the membrane protein channel 321, the hydrogen ions 31 are concentrated near the membrane protein channel 321. The density of the hydrogen ions is higher at position (2) on the lipid bilayer 32. When the probe 200 scans from position (1) to position (2) and then to position (3), a protruding portion at position (2) can be detected. The position of the membrane protein channel 321 can then be inferred by the higher density of the hydrogen ions.

After the position of the membrane protein channel 321 across the lipid bilayer 32 is accurately determined according to the above detection method, the power supply provides an additional current signal through the probe 200 to the electrode probe to detect the electro-physiological signals at the inner and outer sides of the membrane at this specific area.

Overall, the detection platform of the present invention provides a platform for lipid bilayer formation where the structure of the lipid bilayer formed can be supported. Since the stability of the lipid bilayer is improved; thus, the lipid bilayer can be scanned by an atomic force microscope. The probe of the present invention has a nano scale metal tip portion. When detecting the electro-physiological signals at the inner and outer sides of the membrane, the area for detection may be narrowed to a specific small area. The noises from the other areas of the membrane can also be reduced effectively as well.

Accordingly, the membrane electrochemical signal detection system provided by the present invention can solve the difficulties in the positioning of the protein transport channels and the confirmation of their structures. The detection system can be further combined with structural analysis techniques, such as X-ray crystallography, to analyze the position and structure of the protein transport channel. For example, according to an embodiment of the present invention, this novel detection system is able to help researchers to understand H⁺-PPase. The physiological mechanism of the hydrogen ions transportation, the structure of the transport channel, and other issues such as the titration of transport of the H⁺-PPase can be studied.

Although the present invention has been explained in relation to its preferred embodiment, it is to be understood that many other possible modifications and variations can be made without departing from the spirit and scope of the invention as hereinafter claimed.

What is claimed is:

1. A membrane electrochemical signal detection system, comprising a detecting platform and a probe;
   Wherein, the detecting platform comprises:
   a substrate having a cavity;
   a hydrogel layer disposed in the cavity of the substrate;
   a carrier film disposed above the substrate and the hydrogel layer and having at least one through hole corresponding to the cavity of the substrate as a sample slot;
   a gap between the carrier film and the hydrogel layer, wherein the gap is 50 nm~1 µm; and
   the probe is covered by an insulating layer and a metal for detection is exposed at a tip portion of the probe.

2. The membrane electrochemical signal detection system as claimed in claim 1, wherein the system further comprises an atomic force microscope.

3. The membrane electrochemical signal detection system as claimed in claim 1, further comprising a power supply, which provides a current signal or a voltage signal to the probe.

4. The membrane electrochemical signal detection system as claimed in claim 3, further comprising an electrode, which is disposed beneath the hydrogel layer.

5. The membrane electrochemical signal detection system as claimed in claim 1, wherein a thickness of the carrier film is 20 nm~500 nm.

6. The membrane electrochemical signal detection system as claimed in claim 1, wherein a volume of a sample slot is 0.1 nL~10 nL.

7. The membrane electrochemical signal detection system as claimed in claim 1, wherein a thickness of the insulating layer is 10 nm~100 nm.

8. The membrane electrochemical signal detection system as claimed in claim 1, wherein the metal for detection is selected from the group consisting of platinum, iridium, cobalt, palladium, rhodium, and alloys thereof.

9. The membrane electrochemical signal detection system as claimed in claim 1, wherein an exposed area of the metal for detection is 100 nm²~2 µm².

* * * * *